United States Patent [19]

Udovich

[11] Patent Number: 4,876,379

[45] Date of Patent: Oct. 24, 1989

[54] OXIDATIVE ALKOXYCARBONYLATION OF AMINES AND AMINE DERIVATIVES

[75] Inventor: Carl A. Udovich, Joliet, Ill.

[73] Assignee: Amoco Corporation, Chicago, Ill.

[21] Appl. No.: 269,237

[22] Filed: Nov. 9, 1988

Related U.S. Application Data

[63] Continuation of Ser. No. 101,126, Sep. 21, 1987, abandoned.

[51] Int. Cl.$^4$ .......................................... C07C 125/073
[52] U.S. Cl. ..................................... 560/158; 560/24; 560/25
[58] Field of Search ............................ 560/24, 25, 158

[56] References Cited

U.S. PATENT DOCUMENTS

| | | | |
|---|---|---|---|
| 4,178,455 | 12/1979 | Hirai | 560/24 |
| 4,260,781 | 4/1981 | Harvey | 560/24 |
| 4,297,501 | 10/1981 | Becker | 560/24 |
| 4,304,922 | 12/1981 | Becker | 560/24 |
| 4,582,923 | 4/1986 | Stummann | 560/24 |
| 4,621,149 | 11/1986 | Fukuoka | 560/24 |

FOREIGN PATENT DOCUMENTS

| | | | |
|---|---|---|---|
| 71835 | 2/1983 | European Pat. Off. | 560/24 |
| 83096 | 7/1983 | European Pat. Off. | 560/24 |

*Primary Examiner*—Michael L. Shippen
*Attorney, Agent, or Firm*—Reed F. Riley; William H. Magidson; Ralph C. Medhurst

[57] ABSTRACT

The catalyzed oxidative alkoxycarbonylation of amines and substituted amines to form carbamates is disclosed. The process involves alkoxycarbonylation in the presence of a palladium-based catalyst using carbon monoxide, an alkanol and an oxygen-transer agent.

8 Claims, No Drawings

OXIDATIVE ALKOXYCARBONYLATION OF AMINES AND AMINE DERIVATIVES

This is a continuation of application Ser. No. 101,126, filed Sept. 21, 1987 now abandoned.

BACKGROUND OF THE INVENTION

This invention relates to a process for the catalyzed oxidative alkoxycarbonylation of an amine or a substituted amine to form a carbamate and, more particularly, it relates to the elevated temperature and pressure oxidative alkoxycarbonylation of an amine or substituted amine in the presence of a palladium-based catalyst using carbon monoxide, an alkanol and an ioxygen-transfer agent to form an alkyl carbamate.

Alkyl carbamates, such as methyl N-phenylcarbamate, can be readily thermally decomposed to the corresponding isocyanate. If the structure of the material is such that two alkyl carbamate groups are present, thermal decomposition can yield a diisocyanate. A number of these diisocyanate compounds are useful monomers for making commercially useful polyurethanes. For example, toluene diisocyanate is an intermediate in the preparation of high performance polyurethane polymers.

The industrial preparation of isocyanates and polyisocyanates usually involves the use of phosgene, a chemical which has some undesirable features such as toxicity, cost and inclusion of undesirable halogen in the preparation process. The commercial process in use today involves treatment of the appropriate amine feedstock with phosgene. If alkyl carbonates could be made efficiently and cheaply, the use of phosgene in the manufacture of isocyanates could be avoided with consequent elimination of a substantial industrial hazard.

Recently, Asahi Chemical Industry has reported the conversion of amines to carbamates by oxidative carbonylation of an amine in the presence of catalytic amounts of palladium and iodine using an alcohol, oxygen and carbon monoxide. See S. Fukuoka et al., J. Chem. Soc. Chem. Commun. 399 (1984) and Chemtech 670–76 (1984). This method however has some limitations. The presence of elemental oxygen in contact with the organic mixture poses potential safety questions, and the amine starting materials can be hard to purify. So, a more easily purifiable starting material could be beneficial, as long as it forms the corresponding carbamate in high yield. In addition, other ways of supplying the necessary oxygen could answer the safety issue referred to above.

Now it has been found that several significantly broad classes of starting materials based upon amines can be effectively converted to carbamates by a process similar to that described by Fukuoka et al., and several oxygen transfer agents other than oxygen have been shown to convert these classes of materials as well as amines to the corresponding carbamates.

BRIEF DESCRIPTION OF THE INVENTION

Described herein is a process for the oxidative alkoxycarbonylation of a substance selected from compounds containing at least one —NHR radical, wherein R is selected from the group consisting of

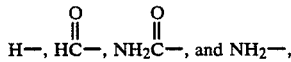

which process comprises combining, at elevated temperature and pressure in the presence of a catalyst comprising a palladium compound, said substance with a $C_1$ to $C_3$ alkanol, an organic or heavy-metal-oxide, oxygen-transfer agent, and carbon monoxide to form a compound containing at least one

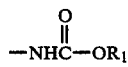

group, wherein $R_1$ is methyl, ethyl, propyl, or isopropyl.

In another aspect, the invention described herein is a process for the oxidative alkoxycarbonylation of a substance selected from compounds containing at least one —NHR radical, wherein R is selected from the group consisting of

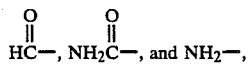

which process comprises combining, at elevated temperature and pressure in the presence of a catalyst comprising a palladium compound, said substance with a $C_1$ to $C_3$ alkanol, oxygen or air, and carbon monoxide to form a compound containing at least one

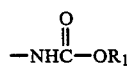

group, wherein $R_1$ is methyl, ethyl, propyl, or isopropyl.

DETAILED DESCRIPTION OF THE INVENTION

Nitrogen-containing compound feeds to one of the processes of the instant invention are usefully aliphatic and aromatic amines and substituted amines having functionality as represented by

and

Such amines and substituted amines contain one or more amino, formamido, carbamido or hydrazino groups. Some representative compounds are aniline, toluidine, phenylene or tolylene diamine, formanilide, phenylene or tolylene diformamide, N-phenylurea, phenylene or tolylene diurea, phenyl hydrazine, phenylene or tolylene dihydrazine, compounds of formula $R(NHCOH)_2$, wherein R is an alkylene group, —$(CH_2)$—$_x$, in which x runs between two and six, and the like.

Preferred are such amines and substituted amines having two such functional groups per molecule, although materials having one, three or even four such groups are useful. In another aspect of the invention all these feeds other than the amines are useful and the feeds having two functional groups of the type listed above per molecule are preferred.

The oxygen-transfer agent in one aspect of the instant invention is air or oxygen. In another aspect of the instant invention, it is an organic oxygen-transfer agent or an inorganic heavy metal oxide. Preferred are oxygen-transfer agents such as nitrobenzene, nitrosobenzene, pyridine N-oxide, silver oxide and mercury oxide. Nitrobenzene and pyridine N-oxide as oxygen-transfer agents are most preferred. An important aspect of the oxygen-transfer agent useful herein is that it be able to part with and reaccept its oxygen easily and to be able to transfer it to the N-containing feed to form carbamate in high yield. It should not appreciably decompose before reaction or interfere appreciably with carbamate formation by decomposing the N-containing starting material, the oxygen-transfer agent, or the catalyst. Normally, the oxygen-transfer agent is used in roughly stoichiometric amount based upon the N-containing feed material used. A slight percent excess of the amount of oxygen-transfer agent over the amount of N-containing material is more preferred.

The processes of the instant invention are catalyzed processes wherein a palladium compound or mixtures thereof with another metal salt is the preferred catalyst. Useful palladium compounds include palladium halides, sulfates, nitrates, acetates, acetylacetonates and the like. Also, one of these palladium compounds can be mixed with varying amounts of an iron, molybdenum, or vanadium salt. Preferred is the use of palladium chloride alone or in mixture with a salt of one of the metals described above. Most preferred is the use of palladium chloride. Normally, only trace amounts of catalyst need be employed.

The alcohols useful herein are any lower alkanol and, preferably, an alkanol selected from the group consisting of methanol, ethanol, propanol and isopropanol. More preferred is the use of methanol. Since it is preferred to run the reaction in the liquid phase, use of excess alkanol as a solvent for the reaction is a very convenient device. If a solvent other than the alcohol employed is used, the amount of alkanol used is at least the stoichiometric amount based on the amount of carbamate to be produced.

Carbon monoxide is normally used without a high degree of purification and is generally used in rather large excess compared to the amounts of N-containing feed and oxygen-transfer agent employed. In batch reactions, the N-containing feed, oxygen transfer agent and catalyst are generally first admixed, and the carbon monoxide pressured in up to a value which yields the desired pressure at reaction temperature.

The reaction can be carried out in the liquid phase either batchwise or continuously. It is preferred to employ a corrosion-resistant reactor, generally in an agitated mode. In either type of operation, the catalyst and oxygen-transfer agent, after separation from the product, may be recycled to the reactor after the oxygen-transfer agent is reoxidized. When oxygen or air is used as the oxygen-transfer agent, there is no reoxidation requirement and a process simplification results.

Reaction pressures desirably lie above about 200 psi and lower than about 2000 psi, and, more preferably lie between about 500 psi and 1000 psi. Preferred reaction temperatures correspondingly lie between about 100° C. and about 300° C., and, more preferably, lie between about 100° C. and about 200° C.

The following Examples will serve to illustrate certain specific embodiments of the herein disclosed invention. These Examples should not, however, be construed as limiting the scope of the novel invention as there are many variations which may be made thereon without departing from the spirit of the disclosed invention, as those of skill in the art will recognize. as those of skill in the art will recognize.

EXAMPLES

General

The oxidative alkoxycarbonylation reactions were carried out in batch fashion in a 300 cc 316 s.s. autoclave equipped with a glass sleeve insert. Liquid and solid reactants were precharged to the autoclave (60 g of methanol was used in each run) which was then repeatedly degased with carbon monoxide or nitrogen to ensure an oxygen-free system. Matheson 99.5% c.p. carbon monoxide was subsequently charged to the autoclave at ambient temperature to a value which would ensure about a 1500 psig operating pressure at maximum temperature. Products were analyzed by liquid chromatography. In the following Examples, Ph is used to designate the phenyl group. The oxygen-transfer agents used in Examples 1–3 below are nitrobenzene, pyridine N-oxide and HgO respectively.

EXAMPLE 1

TABLE 1

Oxidative Carbonylation of Various Materials with Nitrobenzene and Methanol

| N—Containing Compound (1,2) | Catalyst (3) | T (max) °C. | P (max) Psi | Yield of Carbamate Wt. % (4) |
|---|---|---|---|---|
| Phenylamine | $FeCl_3/PdCl_2$ | 313 | 1510 | 97 |
| Phenylamine | $VOCl_3/PdCl_2$ | 300 | 1470 | 107 |
| Formanilide | $FeCl_3/PdCl_2$ | 289 | 1570 | 127 |
| $(PhNH)_2CO$ | $FeCl_3/PdCl_2$ | 314 | 1510 | >100 |
| $(PhNH)_2$ | $FeCl_3/PdCl_2$ | 301 | 1290 | 95 |

(1) In each case 0.1 mol of N—containing compound was employed.
(2) Mol ratio of N—containing compound to nitrobenzene was about 2.
(3) About 6 millimoles total of catalyst was used--3 millimols of the palladium compound and 3 millimols of the iron or vanadium compound.
(4) Yields are based upon a 2:1, nitrogen-containing starting compound to product carbamate stoichiometry. Yields above 100% are due to experimental difficulties encountered in the run.

EXAMPLE 2

TABLE 2

Oxidative Carbonylation of Various Materials with Pyridine N—Oxide and Methanol (1)

| N—Containing Compound (1) | Catalyst (2) | T (max) °C. | P (max) Psi | Yield of Carbamate Wt. % (3) |
|---|---|---|---|---|
| Phenylamine | $PdCl_2$ | 302 | 1220 | 47 |
| Phenylamine | $PdCl_2$ | 307 | 690 | 82 |
| $(PhNH)_2$ | $PdCl_2$ | 323 | 1490 | 88 |
| PhNHCHO | $PdCl_2$ | 307 | 670 | 54 |
| $(PhNH)_2CO$ | $PdCl_2$ | 302 | 650 | 67 |

(1) Mols N—containing compound used and mol ratio, N—containing compound to oxygen-transfer agent same as in Example 1.
(2) A 3 millimols portion of $PdCl_2$ was used in each run.
(3) Yields are based upon a 1:1, nitrogen-containing starting compound to product carbamate stoichiometry.

EXAMPLE 3

TABLE 3

Oxidative Alkoxycarbonylation of Various Materials with HgO and Methanol

| N—Containing Compound (1) | Catalyst (2) | T max °C. | P max Psi | Yield of Carbamate Wt. % (3) |
|---|---|---|---|---|
| PhNHCHO | $PdCl_2$ | 304 | 1340 | 8 |
| $(PhNH)_2$ | $PdCl_2$ | 301 | 1380 | 0 |
| $(PhNH)_2CO$ | $PdCl_2$ | 305 | 1320 | 46 |
| Phenylamine | $PdCl_2$ | 305 | 1300 | 3 |

(1) Mol N—containing compound used and mol ratio, N—containing compound to oxygen transfer agent used, are the same as in Example 1.
(2) A 3 millimols portion of $PdCl_2$ was used in each run.
(3) Yields are based upon a 1:1, nitrogen-containing starting compound to product carbamate stoichiometry.

What is claimed is:

1. In an elevated temperature and pressure process for making a carbamate by carbonylating a substance selected from the group consisting of phenylene or tolylene diamine, phenylene or tolylene diformamide, phenylene or tolylene diurea, phenylene or tolylene dihydrazine, and compounds of formula $R(NHCOH)_2$, wherein R is an alkylene group, $—(CH_2)_x—$, in which x runs between two and six, with carbon monoxide in the presence of a $C_1$ to $C_3$ alkanol, an oxygen transfer agent, and a catalyst comprising a palladium compound, the improvement which uses pyridine N-oxide as said oxygen-transfer agent.

2. The process of claim 1 wherein said $C_1$ to $C_3$ alkanol is methanol.

3. The process of claim 2 wherein said catalyst comprises palladium chloride.

4. The process of claim 3 wherein said substance is a compound of formula $R_2(NHCOH)_2$ wherein $R_2$ is an alkenylene group, $—(CH_2)_x—$, in which x runs between two and six.

5. The process of claim 1 wherein the deoxygenated form of said oxygen-transfer agent is reoxidized after transfer of its oxygen.

6. The process of claim 4 wherein the deoxygenated form of said oxygen-transfer agent is reoxidized after transfer of its oxygen.

7. The process of claim 1 wherein said elevated temperature lies between about 100° C. and about 300° C. and said elevated pressure lies between about 200 psi and about 2000 psi.

8. The process of claim 6 wherein said elevated temperature lies between about 100° C. and about 300° C. and said elevated pressure lies between about 200 psi and about 2000 psi.

* * * * *